United States Patent
Kim et al.

(10) Patent No.: US 11,246,560 B2
(45) Date of Patent: Feb. 15, 2022

(54) ULTRASOUND PROBE, ULTRASOUND IMAGING APPARATUS, ULTRASOUND IMAGING SYSTEM, AND METHOD FOR CONTROLLING THEREOF

(71) Applicants: SAMSUNG MEDISON CO., LTD., Gangwon-do (KR); SOGANG UNIVERSITY RESEARCH FOUNDATION, Seoul (KR)

(72) Inventors: Kang Sik Kim, Seongnam-si (KR); Tae-kyong Song, Seoul (KR); Ji Won Park, Seoul (KR)

(73) Assignee: SAMSUNG MEDISON CO., LTD., Ganwon-Do (KR)

( * ) Notice: Subject to any disclaimer, the term of this patent is extended or adjusted under 35 U.S.C. 154(b) by 400 days.

(21) Appl. No.: 16/338,610

(22) PCT Filed: Aug. 9, 2017

(86) PCT No.: PCT/KR2017/008619
§ 371 (c)(1),
(2) Date: Apr. 1, 2019

(87) PCT Pub. No.: WO2018/056572
PCT Pub. Date: Mar. 29, 2018

(65) Prior Publication Data
US 2019/0298299 A1    Oct. 3, 2019

Related U.S. Application Data

(60) Provisional application No. 62/397,269, filed on Sep. 20, 2016.

(30) Foreign Application Priority Data

Dec. 9, 2016  (KR) .................. 10-2016-0167325

(51) Int. Cl.
*A61B 8/06* (2006.01)
*A61B 8/14* (2006.01)
(Continued)

(52) U.S. Cl.
CPC .............. *A61B 8/06* (2013.01); *A61B 5/026* (2013.01); *A61B 8/145* (2013.01); *A61B 8/4472* (2013.01);
(Continued)

(58) Field of Classification Search
CPC ... A61B 8/485; A61B 8/5276; G01S 15/8977; G01S 15/8993
(Continued)

(56) References Cited

U.S. PATENT DOCUMENTS 6,279,398 B1    8/2001  Bae et al.
2009/0326379 A1   12/2009  Daigle et al.
(Continued)

FOREIGN PATENT DOCUMENTS

| JP | 2016-086876 A | 5/2016 |
| KR | 10-1570194 B1 | 11/2015 |
| KR | 10-1652727 B1 | 9/2016 |

OTHER PUBLICATIONS

Ekroll et al., "Simultaneous Quantification of Flow and Tissue Velocities Based on Multi-Angle Plane Wave Imaging" IEEE Transactions on Ultrasonics, Ferroelectrics, and Frequency Control, vol. 60, No. 4, Apr. 2013, pp. 727-735 (Year: 2013).*
(Continued)

*Primary Examiner* — Boniface N Nganga
(74) *Attorney, Agent, or Firm* — Morgan, Lewis & Bockius LLP

(57) ABSTRACT

Provided are an ultrasound probe, an ultrasound imaging apparatus, an ultrasound imaging system including the ultrasound imaging apparatus, and a method of controlling the
(Continued)

ultrasound imaging apparatus. In accordance with one aspect, the ultrasound probe includes a transducer configured to receive an echo ultrasound signal by emitting a plane wave at least three times at different emission angles or at emission angles which are dependent on each other; and a probe controller configured to obtain an ultrasound image by determining a Doppler shift frequency from the received echo ultrasound signal and calculating at least one of a speed of an object and a speed of the object in each of directions on the basis of the determined Doppler shift frequency and either the different emission angles or the dependent emission angles.

15 Claims, 15 Drawing Sheets

(51) Int. Cl.
*A61B 8/00* (2006.01)
*A61B 8/08* (2006.01)
*A61B 5/026* (2006.01)

(52) U.S. Cl.
CPC .......... *A61B 8/488* (2013.01); *A61B 8/5223* (2013.01); *A61B 8/54* (2013.01); *A61B 8/4405* (2013.01); *A61B 8/4427* (2013.01); *A61B 8/4488* (2013.01); *A61B 8/467* (2013.01); *A61B 8/5207* (2013.01)

(58) Field of Classification Search
USPC .......................................................... 600/454
See application file for complete search history.

(56) References Cited

U.S. PATENT DOCUMENTS

| | | | |
|---|---|---|---|
| 2012/0226160 A1* | 9/2012 | Kudoh | A61B 8/546 600/443 |
| 2014/0371594 A1 | 12/2014 | Flynn et al. | |
| 2015/0065882 A1* | 3/2015 | Cho | A61B 8/5207 600/443 |
| 2015/0141832 A1 | 5/2015 | Yu et al. | |

OTHER PUBLICATIONS

Extended European Search Report dated Apr. 22, 2020 issued in European Patent Application No. 17853286.7.
J. Flynn, et al., "Estimation and Display for Vector Doppler Imaging Using Planewave Transmissions," Ultrasonic Symposium, 2011 IEEE International, IEEE, Oct. 18, 2011, pp. 413-418.
International Search Report dated Nov. 17, 2017 issued in International Patent Application No. PCT/KR2017/008619.

* cited by examiner

ULTRASOUND PROBE, ULTRASOUND IMAGING APPARATUS, ULTRASOUND IMAGING SYSTEM, AND METHOD FOR CONTROLLING THEREOF

CROSS-REFERENCE OF RELATED APPLICATIONS

This application is the U.S. National Phase under 35 U.S.C. § 371 of International Patent Application No. PCT/KR2017/008619, filed on Aug. 9, 2017, which in turn claims the benefit of U.S. Provisional Patent Application No. 62/397,269, filed on Sep. 20, 2016 and Korean Patent Application No. 10-2016-0167325, filed Dec. 9, 2016, the entire disclosures of which applications are incorporated by reference herein.

TECHNICAL FIELD

Provided are an ultrasound probe for obtaining an ultrasound image, an ultrasound imaging apparatus for providing the obtained ultrasound image, an ultrasound imaging system including the ultrasound imaging apparatus, and a method of controlling the ultrasound imaging apparatus.

DISCLOSURE

Technical Problem

An ultrasound imaging system which is one of major imaging systems which have been variously applied has non-invasive and non-destructive characteristics and has thus been widely used in the medical field. The ultrasound imaging system obtains and displays a two-dimensional (2D) or three-dimensional (3D) ultrasound image of the inside of an object using an ultrasound probe and thus the object may be diagnosed.

Recently, research has been conducted on increasing the accuracy of an ultrasound image to accurately diagnose an object.

Technical Solution

Provided are an ultrasound probe for obtaining an ultrasound image more accurately reflecting a motion of an object, an ultrasound imaging apparatus, an ultrasound imaging system, and a method of controlling the ultrasound imaging apparatus.

In accordance with an aspect of an embodiment, an ultrasound probe includes a transducer configured to receive an echo ultrasound signal by emitting a plane wave at least three times either at different emission angles or at emission angles which are dependent on each other; and a probe controller configured to obtain an ultrasound image by determining a Doppler shift frequency from the received echo ultrasound signal and calculating at least one of a speed of an object and a speed of the object in each of directions on the basis of the determined Doppler shift frequency and either the different emission angles or the dependent emission angles.

The probe controller may control the transducer to emit the plane wave at least three times at the different emission angles, determine the Doppler shift frequency from the echo ultrasound signal received by emitting the plane wave at least three times, calculate a blood flow speed and direction of the object on the basis of the determined Doppler shift frequency and the different emission angles, and obtain the ultrasound image on the basis of the calculated blood flow speed and direction of the object.

The probe controller may control the transducer to emit the plane wave at least four times at the dependent emission angles, determine the Doppler shift frequency from the echo ultrasound signal received by emitting the plane wave at least four times, determine a blood flow speed of the object in each of the directions on the basis of the determined Doppler shift frequency and the dependent emission angles, and obtain information regarding a blood flow speed of the object on the basis of the determined blood flow speed of the object in each of the directions.

The different emission angles may be represented by two angle parameters. The two angle parameters of each of the different emission angles may be set to be different from those of the other emission angles.

The dependent emission angles may be represented by two angle parameters. One of the two angle parameters of each of the dependent emission angles may be set to be the same as ones of the two angle parameters of the other emission angles.

The dependent emission angles may be represented by two angle parameters. One of the two angle parameters of each of the dependent emission angles may be set to be the same as ones of the two angle parameters of the other emission angles, and the other angle parameter of each of the dependent emission angles may be set to be spaced apart from the other angle parameters of the other emission angles according to a predetermined angle.

In accordance with another aspect of an embodiment, an ultrasound imaging apparatus includes a communication unit configured to receive an echo ultrasound signal reflected from an object when a plane wave is emitted at least three times either at different emission angles or at emission angles which are dependent on each other; and a main controller configured to obtain an ultrasound image by determining a Doppler shift frequency from the received echo ultrasound signal and calculating at least one of a speed of an object and a speed of the object in each of directions on the basis of the determined Doppler shift frequency and either the different emission angles or the dependent emission angles.

The main controller may control the communication unit to transmit a control signal for emitting the plane wave at least three times at the different emission angles, determine the Doppler shift frequency from the received echo ultrasound signal, calculate a blood flow speed and direction of the object on the basis of the calculated Doppler shift frequency and the different emission angles, and obtain the ultrasound image on the basis of the determined blood flow speed and direction of the object.

The main controller may control the communication unit to transmit a control signal for emitting the plane wave at least four times at the dependent emission angles, determine the Doppler shift frequency from the received echo ultrasound signal, determine a blood flow speed of the object in each of the directions on the basis of the determined Doppler shift frequency and the dependent emission angles, and obtain information regarding a blood flow speed of the object on the basis of the determined blood flow speed of the object in each of the directions.

The different emission angles may be represented by two angle parameters. The two angle parameters of each of the different emission angles may be set to be different from those of the other emission angles.

The dependent emission angles may be represented by two angle parameters. One of the two angle parameters of each of the dependent emission angles may be set to be the same as ones of the two angle parameters of the other emission angles.

The dependent emission angles may be represented by two angle parameters. One of the two angle parameters of each of the dependent emission angles may be set to be the same as ones of the two angle parameters of the other emission angles, and the other angle parameter of each of the dependent emission angles may be set to be spaced apart from the other angle parameters of the other emission angles according to a predetermined angle.

According to another aspect of an embodiment, a method of controlling an ultrasound imaging apparatus includes receiving an echo ultrasound signal reflected from an object when a plane wave is emitted at least three times either at different emission angles or at emission angles which are dependent on each other; and obtaining an ultrasound image by determining a Doppler shift frequency from the received echo ultrasound signal and calculating at least one of a speed of an object and a speed of the object in each of directions on the basis of the determined Doppler shift frequency and either the different emission angles or the dependent emission angles.

The obtaining of the ultrasound image may include determining the Doppler shift frequency from the received echo ultrasound signal, calculating a blood flow speed and direction of the object on the basis of the determined Doppler shift frequency and the different emission angles, and obtaining the ultrasound image on the basis of the calculated blood flow speed and direction of the object.

The obtaining of the ultrasound image may include determining the Doppler shift frequency from the received echo ultrasound signal, determining a blood flow speed of the object in each of the directions on the basis of the determined Doppler shift frequency and the dependent emission angles, and obtaining information regarding a blood flow speed of the object on the basis of the determined blood flow speed of the object in each of the directions.

The different emission angles may be represented by two angle parameters. The two angle parameters of each of the different emission angles may be set to be different from those of the other emission angles.

The dependent emission angles may be represented by two angle parameters. One of the two angle parameters of each of the dependent emission angles may be set to be the same as ones of the two angle parameters of the other emission angles.

The dependent emission angles may be represented by two angle parameters. One of the two angle parameters of each of the dependent emission angles may be set to be the same as ones of the two angle parameters of the other emission angles, and the other angle parameter of each of the dependent emission angles may be set to be spaced apart from the other angle parameters of the other emission angles according to a predetermined angle.

Advantageous Effects

In an ultrasound probe, an ultrasound imaging apparatus, an ultrasound imaging system, and a method of controlling the ultrasound imaging apparatus in accordance with an embodiment, an ultrasound image more accurately reflecting a speed of an object in each of directions and a speed of the object may be obtained from an echo ultrasound signal received by emitting a plane wave at different emission angles or at emission angles dependent on each other.

In an ultrasound probe, an ultrasound imaging apparatus, an ultrasound imaging system, and a method of controlling the ultrasound imaging apparatus in accordance with another embodiment, the number of regions of an object, images of which may be obtained may be increased by emitting a plane wave at various emission angles.

MODE FOR INVENTION

Hereinafter, embodiments will be described in detail with reference to the accompanying drawings.

Figure 1:
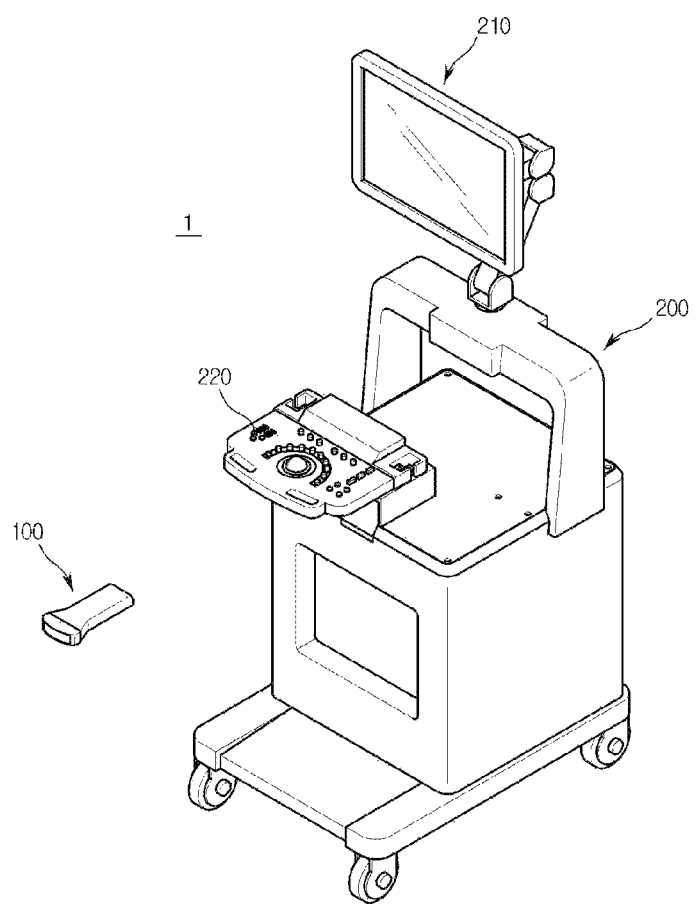
FIG. 1 is a diagram illustrating an external structure of an ultrasound imaging system including an ultrasound probe and an ultrasound imaging apparatus connected to the ultrasound probe according to a wired or wireless communication method, in accordance with an embodiment.
Figure 2:
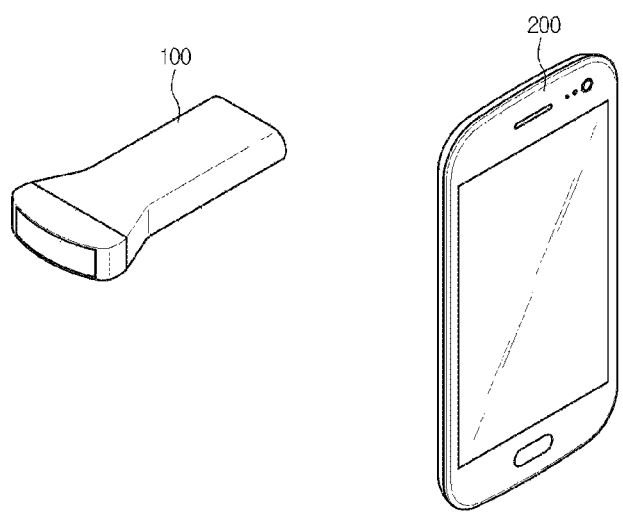
FIG. 2 is a diagram illustrating an external structure of an ultrasound imaging system including an ultrasound imaging apparatus embodied differently from the ultrasound imaging apparatus of FIG. 1, in accordance with another embodiment.

FIG. 1 is a diagram illustrating an external structure of an ultrasound imaging system including an ultrasound probe and an ultrasound imaging apparatus connected to the ultrasound probe according to a wired or wireless communication method, in accordance with an embodiment. FIG. 2 is a diagram illustrating an external structure of an ultrasound imaging system including an ultrasound imaging apparatus embodied differently from the ultrasound imaging apparatus of FIG. 1, in accordance with an embodiment. FIGS. 1 and 2 will be described together below to avoid redundancy.

Referring to FIG. 1, an ultrasound imaging system 1 includes an ultrasound probe 100 which emits an ultrasound signal to an object, receives an echo ultrasound signal from the object, and converts the echo ultrasound signal into an electrical signal, and an ultrasound imaging apparatus 200 which is connected to the ultrasound probe 100 according to a wired/wireless communication method and displays an ultrasound image.

The ultrasound probe 100 may be connected to the ultrasound imaging apparatus 200 according to the wired communication method to receive various signals for controlling the ultrasound probe 100 from the ultrasound imaging apparatus 200. Furthermore, the ultrasound probe 100 may transmit to the ultrasound imaging apparatus 200 either an analog signal or a digital signal corresponding to a received echo ultrasound signal or an ultrasound image reconstructed from the echo ultrasound signal.

Here, the wired communication method refers to a communication method of transmitting or receiving a signal containing data via wire. Examples of the wired communication method include a peripheral component interconnect (PCI), PCI-express, a universal serial bus (USB), etc. but are not limited thereto and may include already known various other methods.

Alternatively, the ultrasound probe 100 may be connected to the ultrasound imaging apparatus 200 according to the wireless communication method to receive various signals for controlling the ultrasound probe 100 from the ultrasound imaging apparatus 200 or to transmit either an analog signal or a digital signal corresponding to an echo ultrasound signal received by the ultrasound probe 100. Furthermore, the ultrasound probe 100 may transmit information regarding an operating state of the ultrasound probe 100 and the like to the ultrasound imaging apparatus 200.

Here, the wireless communication method refers to a communication network supporting a wireless communication method of wirelessly transmitting and receiving a signal. Examples of the wireless communication method include not only communication methods of transmitting or receiving a wireless signal via a base station, such as third generation (3G) and fourth generation (4G), but also communication methods of directly transmitting or receiving a wireless signal between devices within a predetermined distance, such as a wireless local area network (LAN), Wi-Fi, Bluetooth, Zigbee, Wi-Fi direct (WFD), ultra-wideband (UWB), infrared data association (IrDA), Bluetooth low energy (BLE), and near-field communication (NFC).

However, the wireless communication method is not limited thereto and includes all communication networks supporting exchange of a wireless signal between the ultrasound probe 100 and the ultrasound imaging apparatus 200. For convenience of explanation, the wired communication method and the wireless communication method will be hereinafter referred to together as a communication method when there is no need to differentiate them from each other. A wired communication network and a wireless communication network will be hereinafter referred to together as a communication network when there is no need to differentiate them from each other.

The ultrasound imaging apparatus 200 may be embodied in a form generally used in a hospital or the like for an ultrasonic diagnosis as illustrated in FIG. 1. However, the form of the ultrasound imaging apparatus 200 is not limited to that illustrated in FIG. 1.

For example, the ultrasound imaging apparatus 200 may be embodied as not only a laptop computer, a desktop computer, a tablet personal computer (PC) but also as a smartphone illustrated in FIG. 2. As another example, the ultrasound imaging apparatus 200 may be embodied as a mobile terminal such as a personal digital assistant (PDA), a watch which is attachable to and detachable from a user's body, or a glasses-type wearable terminal.

However, the ultrasound imaging apparatus 200 is not limited thereto and may be any type device which includes a communication module therein to exchange a wire/wireless signal with an external device according to at least one of the wireless communication method and the wired communication method and which includes a processor therein to perform various arithmetic operations.

One of forms in which an ultrasound imaging apparatus may be embodied will be described as an example with reference to FIG. 1 below, but the ultrasound imaging apparatus may be embodied in various forms as described above and embodiments which will be described below are thus not limited thereto.

The ultrasound imaging apparatus 200 illustrated in FIG. 1 will be described below. In the ultrasound imaging apparatus 200, a display unit 210 and an input unit 220 may be provided. The input unit 220 may receive setting information regarding the ultrasound probe 100, various control commands, etc. from a user.

In an embodiment, the setting information regarding the ultrasound probe 100 includes gain information, zoom information, focus information, time gain compensation (TGC) information, depth information, frequency information, power information, frame average information, dynamic range information, etc. However, the setting information regarding the ultrasound probe 100 is not limited thereto and may include various information which may be set to obtain an ultrasound image.

In another embodiment, the input unit 220 may receive a control command regarding the ultrasound probe 100 or the ultrasound imaging apparatus 200 from a user. The setting information, the control command, etc. described above may be transmitted to the ultrasound probe 100 via a communication network, and the ultrasound probe 100 may be set according to the transmitted information.

The input unit 220 may be embodied as a keyboard, a foot switch, or a foot pedal. For example, the keyboard may be embodied as hardware. Such a keyboard may include at least one among a switch, a key, a joystick, and a trackball. As another example, the keyboard may be embodied as software, e.g., in the form of a graphical user interface. In this case, the keyboard may be displayed on the display unit 210. The foot switch or the foot pedal may be provided at the bottom of the ultrasound imaging apparatus 200. A user may control an operation of the ultrasound imaging apparatus 200 using the foot pedal.

The display unit 210 may display an ultrasound image of a target inner part of an object. The ultrasound image displayed on the display unit 210 may be a two-dimensional (2D) or three-dimensional (3D) ultrasound image. Various ultrasound images may be displayed according to an operating mode of the ultrasound imaging apparatus 200. Furthermore, the display unit 210 may display not only a menu or information for the ultrasound image but also information regarding an operating state of the ultrasound probe 100, etc.

The display unit 210 may be embodied as, but is not limited to, already-known various display panels, such as a cathode ray tube (CRT), a liquid crystal display (LCD), a light-emitting diode (LED), a plasma display panel (PDP), and an organic light-emitting diode (OLED).

When the display unit 210 is a touch screen type display, the display unit 210 may also perform a function of the input unit 220. That is, a user may input various commands through the display unit 210 or the input unit 220.

For example, virtual input buttons or the like may be displayed on a display of the ultrasound imaging apparatus 200 of FIG. 2 through a graphical user interface and thus a user may input various commands using the virtual input buttons.

A structure of the ultrasound probe 100 will be described in more detail below.

Figure 3:
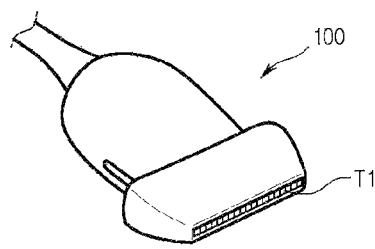
FIG. 3 is a diagram illustrating an exterior of an ultrasound probe having a one-dimensional (1D) transducer array, in accordance with an embodiment.
Figure 4:
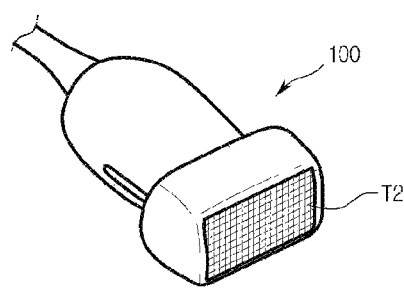
FIG. 4 is a diagram illustrating an exterior of an ultrasound probe having a two-dimensional (2D) transducer array, in accordance with another embodiment.

FIG. 3 is a diagram illustrating an exterior of an ultrasound probe having a one-dimensional (1D) transducer array, in accordance with an embodiment. FIG. 4 is a diagram illustrating an exterior of an ultrasound probe having a 2D transducer array, in accordance with another embodiment. FIGS. 3 and 4 will be described together below to avoid redundancy.

An ultrasound probe 100 is configured to be in contact with a surface of an object, and may emit an ultrasound signal. In detail, the ultrasound probe 100 may emit an ultrasound signal into the object according to a control command signal received from an ultrasound imaging apparatus 200, receive an echo ultrasound signal reflected from a specific inner part of the object, and transmit the echo ultrasound signal to the ultrasound imaging apparatus 200. Thus, the ultrasound probe 100 may transmit an echo ultrasound signal received from the object to the ultrasound imaging apparatus 200 or may obtain an ultrasound image from the echo ultrasound signal and transmit the ultrasound image via a communication network, but is not limited thereto.

In this case, the ultrasound probe 100 may include a transducer which converts an electrical signal into an ultrasound signal or vice versa to transmit an ultrasound wave into an object. The transducer may be embodied as a 1D or 2D transducer array having a plurality of transducer elements.

For example, the transducer may include a 1D transducer array T1 as illustrated in FIG. 3. In another embodiment, the transducer may include a 2D transducer array T2 as illustrated in FIG. 4.

For example, the transducer elements of the 1D transducer array may convert an ultrasound signal into an electrical signal or vice versa. To this end, the transducer elements may be embodied as magnetostrictive ultrasonic transducers using a magnetostrictive effect of a magnetic substance, piezoelectric ultrasonic transducers using a piezoelectric effect of a piezoelectric material, piezoelectric micro-machined ultrasonic transducers (pMUTs), or capacitive micromachined ultrasonic transducers (hereinafter abbreviated as 'cMUTs') which transmit or receive an ultrasound wave using vibration of several hundreds or thousands of micromachined thin films.

The transducers may be arranged linearly or in a convex shape. A basic operating principle of the ultrasound probe 100 is the same when the transducers are arranged linearly or in the convex shape. However, in the ultrasound probe 100 having the transducers arranged in the convex shape, ultrasound waves emitted from the transducers have a fan shape and thus a generated ultrasound image may also have a fan shape.

Referring to FIG. 4, the transducer of the ultrasound probe 100 may include the 2D transducer array T2 as described above. When the 2D transducer array T2 is provided, a 3D image of the inside of an object may be obtained.

The transducer elements of the 2D transducer array are the same as those of the 1D transducer array and are thus not described in detail here. A relationship between the ultrasound probe 100 and the ultrasound imaging apparatus 200 will be described below.

Figure 5:
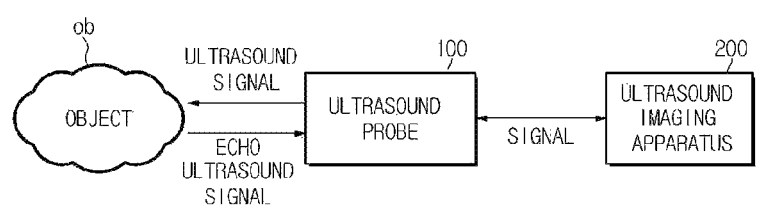
FIG. 5 is a diagram illustrating a relationship between an ultrasound probe and an ultrasound imaging apparatus in accordance with an embodiment.

FIG. 5 is a diagram illustrating a relationship between an ultrasound probe and an ultrasound imaging apparatus in accordance with an embodiment.

An ultrasound system may include an ultrasound probe 100 and an ultrasound imaging apparatus 200. Referring to FIG. 5, the ultrasound system may emit an ultrasound signal from a surface of an object ob toward a target inner part of the body of the object ob using the ultrasound probe 100, noninvasively obtain a tomographic image of soft tissue of the body or an image of a blood flow using an ultrasound signal reflected from the target inner part, i.e., an echo ultrasound signal, and provide a user with the obtained image.

For example, the ultrasound probe 100 may emit a plane wave to an object using the 2D transducer array T2. Here, the plane wave should be understood as an ultrasound signal having a 2D planar shape.

The ultrasound probe 100 may receive an echo ultrasound signal reflected from the object ob by emitting the plane wave to the object, and transmit the received echo ultrasound signal to the ultrasound imaging apparatus 200.

In this case, the ultrasound imaging apparatus 200 may include a main controller which performs an image processing process to convert the received echo ultrasound signal into an ultrasound image. The main controller may be embodied as hardware, such as a processor or a graphic processor, or software which may be executed on hardware. The main controller will be described in detail below.

As another example, the ultrasound probe 100 may directly convert the echo ultrasound signal into an ultrasound image and transmit the ultrasound image to the ultrasound imaging apparatus 200 as described above. The ultrasound probe 100 may include a probe controller embodied as hardware, such as a processor or a graphic processor, or as software which may be executed on hardware to convert the echo ultrasound signal into an ultrasound image. The probe controller will be described in detail below. Thus, the ultrasound probe 100 may transmit the ultrasound image or the echo ultrasound signal to the ultrasound imaging apparatus 200 via a communication network but is not limited thereto.

The generated ultrasound image may be stored in a memory included in the ultrasound imaging apparatus 200. Alternatively, the ultrasound image may be stored in web storage or a cloud server having a storing function on a web. Inner structures of an ultrasound probe and an ultrasound imaging apparatus will be described in more detail below.

Figure 6:
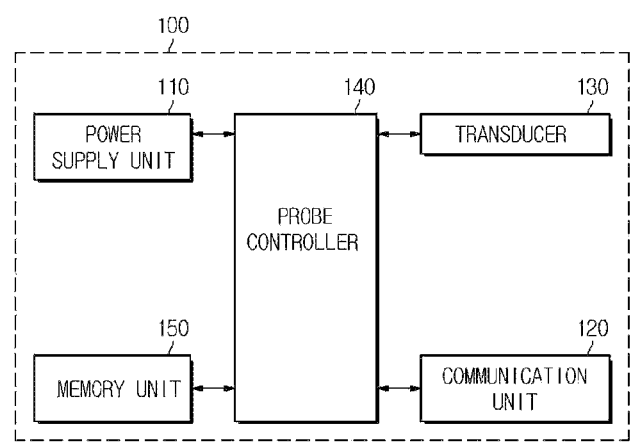
FIG. 6 is a control block diagram of an ultrasound probe in accordance with an embodiment.
Figure 7:
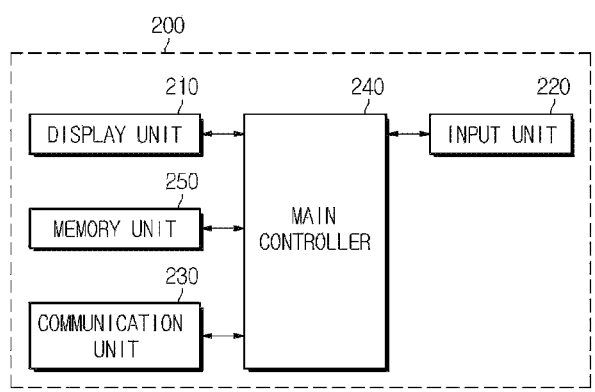
FIG. 7 is a control block diagram of an ultrasound imaging apparatus in accordance with an embodiment.
Figure 8:
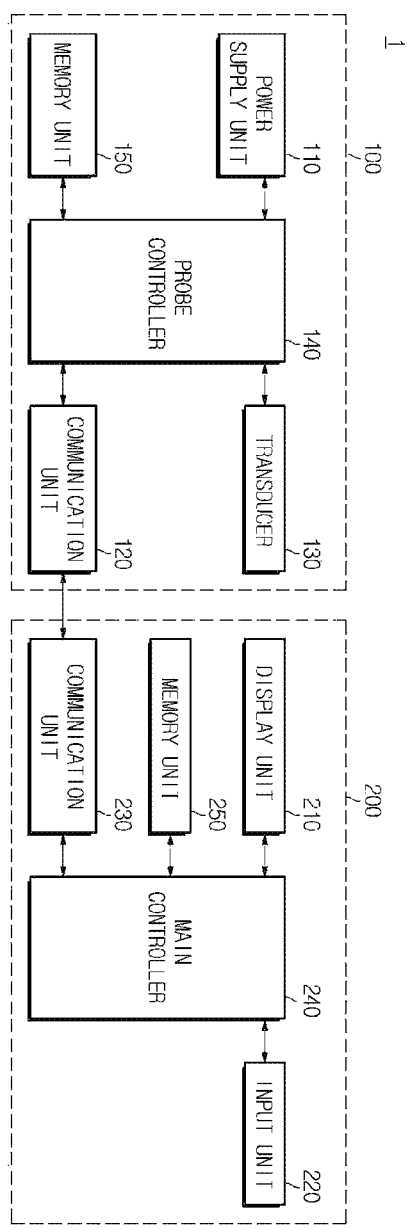
FIG. 8 is a control block diagram of an ultrasound imaging system including an ultrasound probe and an ultrasound imaging apparatus, in accordance with an embodiment.
Figure 9:
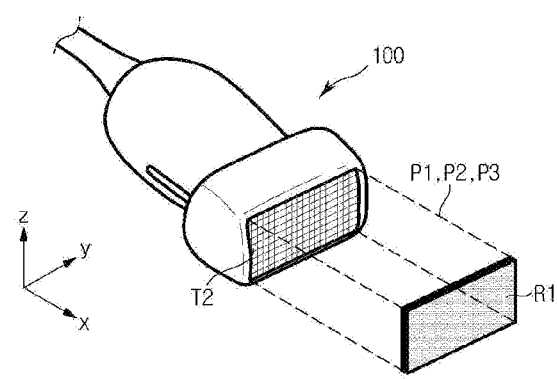
FIG. 9 is a diagram illustrating a region of an object, an image of which may be obtained when a plane wave is emitted several times at the same emission angle in accordance with an embodiment, when viewed at a side.
Figure 10:
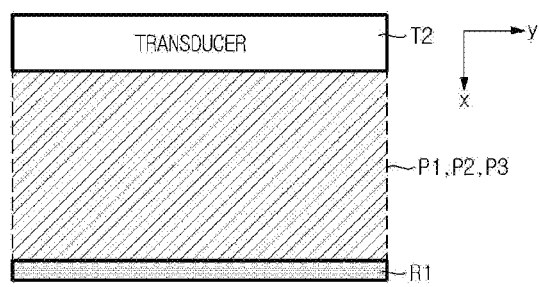
FIG. 10 is a diagram illustrating a region of an object, an image of which may be obtained when a plane wave is emitted several times at the same emission angle in accordance with an embodiment, when viewed at another side.
Figure 11:
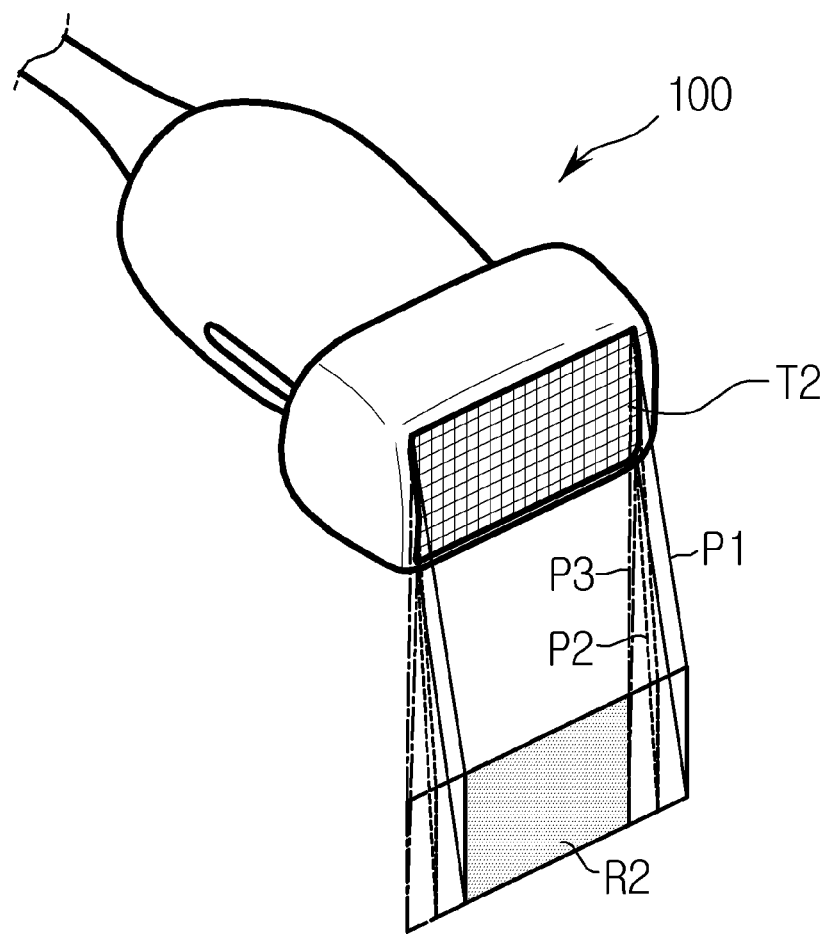
FIG. 11 is a diagram illustrating a region of an object, an image of which may be obtained when a plane wave is emitted at different emission angles in accordance with another embodiment, when viewed at a side.
Figure 12:
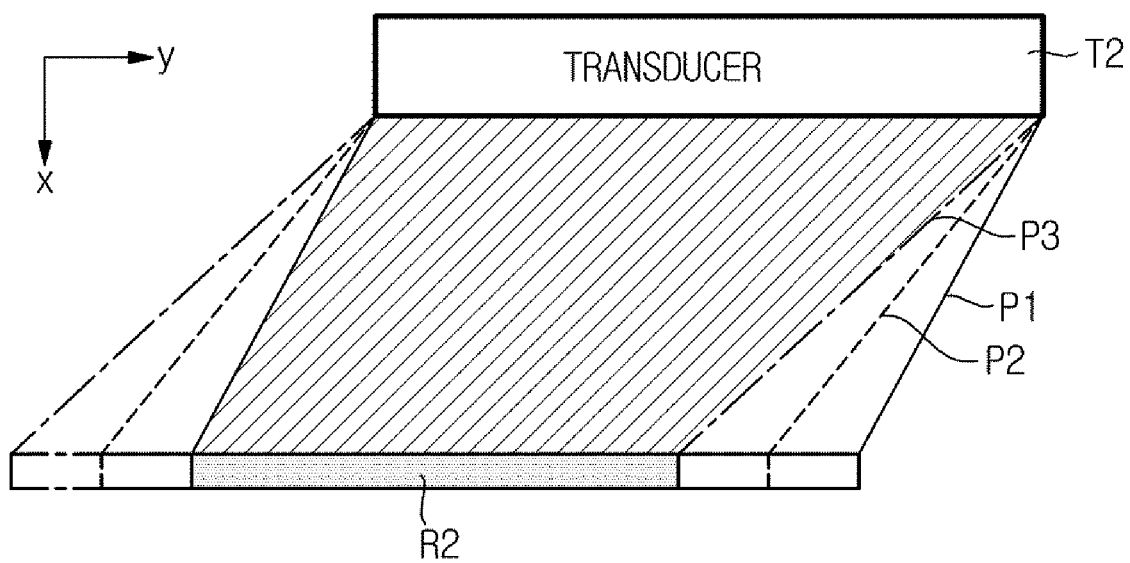
FIG. 12 is a diagram illustrating a region of an object, an image of which may be obtained when a plane wave is emitted at different emission angles in accordance with another embodiment, when viewed at another side.
Figure 13:
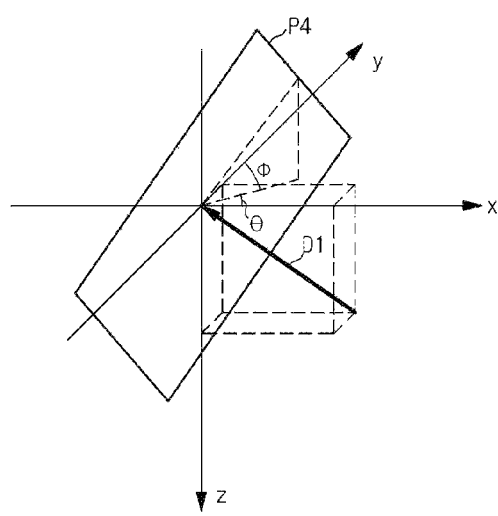
FIG. 13 is a diagram illustrating an angle at which a plane wave is emitted, and an angle at which an echo ultrasound signal is received, in accordance with an embodiment.
Figure 14:
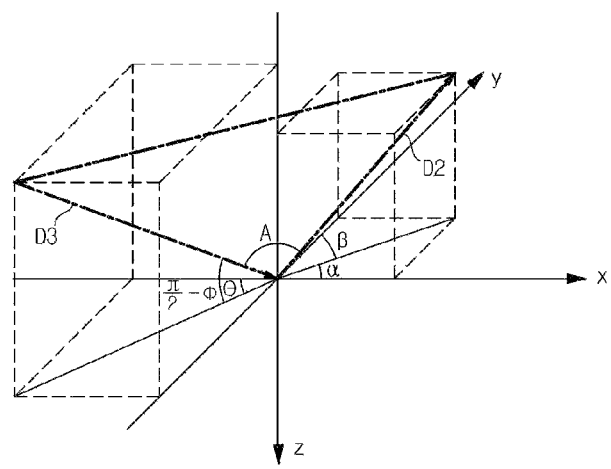
FIG. 14 is a diagram illustrating an angle between a direction of a motion of an object and a direction in which a plane wave is emitted, in accordance with an embodiment.

FIG. 6 is a control block diagram of an ultrasound probe in accordance with an embodiment. FIG. 7 is a control block diagram of an ultrasound imaging apparatus in accordance with an embodiment. FIG. 8 is a control block diagram of an ultrasound imaging system including an ultrasound probe and an ultrasound imaging apparatus, in accordance with an embodiment. FIG. 9 is a diagram illustrating a region of an object, an image of which may be obtained when a plane wave is emitted several times at the same emission angle in accordance with an embodiment, when viewed at a side. FIG. 10 is a diagram illustrating a region of an object, an image of which may be obtained when a plane wave is emitted several times at the same emission angle in accordance with an embodiment, when viewed at another side. FIG. 11 is a diagram illustrating a region of an object, an image of which may be obtained when a plane wave is emitted at different emission angles in accordance with another embodiment, when viewed at a side. FIG. 12 is a diagram illustrating a region of an object, an image of which may be obtained when a plane wave is emitted at different emission angles in accordance with another embodiment, when viewed at another side. FIG. 13 is a diagram illustrating an angle at which a plane wave is emitted, and an angle at which an echo ultrasound signal is received, in accordance with an embodiment. FIG. 14 is a diagram illustrating an angle between a direction of a motion of an object and a direction in which a plane wave is emitted, in accordance with an embodiment. FIGS. 6 to 14 will be described together below to avoid redundancy.

A case in which a probe controller 140 of an ultrasound probe 100 obtains an ultrasound image through an image processing process and transmits it to the ultrasound imaging apparatus 200 will be described below. All or some of operations performed to obtain an ultrasound image may be performed by a main controller 240 of an ultrasound imaging apparatus 200 but embodiments are not limited thereto.

Referring to FIG. 6, the ultrasound probe 100 may include a power supply unit 110 which supplies power to the ultrasound probe 100, a communication unit 120 which transmits various signals to or receives various signals from an external device, a transducer 130 which emits an ultrasound signal to an object and receives an echo ultrasound signal reflected from the object, the probe controller 140 which controls overall operations of the ultrasound probe 100, and a memory unit 150 which stores various types of control data, an echo ultrasound signal, etc. needed to control an operation of the ultrasound probe 100.

Here, at least one among the communication unit 120, the probe controller 140, and the memory unit 150 may be integrated into a system-on-chip (SoC) embedded in the ultrasound probe 100, and may be operated by a processor. In this case, the number of SoCs included in the ultrasound probe 100 is not limited to one and thus at least one among the communication unit 120, the probe controller 140, and the memory unit 150 is not limited to being integrated into one SoC.

The power supply unit 110 may supply power to the ultrasound probe 100. In detail, the power supply unit 110 may supply power by converting electrical energy into chemical energy, accumulating the chemical energy, and converting the accumulated chemical energy into electrical energy. In one embodiment, the power supply unit 110 may be embodied as a lithium ion battery, a nickel metal hydrogen battery, a polymer battery, or the like. However, the power supply unit 110 in accordance with an embodiment is not limited thereto, and may be embodied as various types of batteries which may be embedded in the ultrasound probe 100 to supply power.

The power supply unit 110 may be charged by directly connecting it to a charging device according to a wired charging method or may be charged according to a wireless charging method. That is, a method of charging the power supply unit 110 is not limited, and the power supply unit 110 may be charged according to already known various methods.

When the ultrasound probe 100 is connected to the ultrasound imaging apparatus 200 according to the wired communication method, the power supply unit 110 may be included in the ultrasound probe 100 if necessary but may not be included in the ultrasound probe 100 and is not limited to that illustrated in FIG. 6.

Referring to FIG. 6, the communication unit 120 may be included in the ultrasound probe 100.

The communication unit 120 may include one or more elements for establishing wireless or wired communication with an external device. For example, the communication unit 120 may include at least one of a wireless communication module having at least one among a short-distance communication module and a mobile communication module, and a wired communication module supporting the wired communication method.

The short-distance communication module refers to a module for short-distance communication within a predetermined distance. For example, the short-distance communication may include, but is not limited to, a wireless LAN, Wi-Fi, Bluetooth, Zigbee, Wi-Fi direct (WFD), ultra-wideband (UWB), infrared data association (IrDA), Bluetooth low energy (BLE), near-Field communication (NFC), or the like.

The mobile communication module may exchange wireless signals with at least one among a base station, an external terminal, and a server in a mobile communication network. For example, the mobile communication module may exchange various types of data with the ultrasound imaging apparatus 200 via the base station through a 3G or 4G communication network. The short-distance communication module and the mobile communication module will be hereinafter referred to together as a communication module.

The wired communication module refers to a module supporting exchange of signals containing data via wire. For example, the wired communication module may support at least one among already-known various types of wired communication methods such as peripheral component interconnect (PCI), PCI-express, and a universe serial bus (USB).

The communication unit 120 may exchange various types of data with the ultrasound imaging apparatus 200 through a communication network. The communication unit 120 may transmit or receive data related to diagnosing an object, such as an ultrasound image of the object, echo ultrasound data, Doppler data, etc., through the communication network. Furthermore, the communication unit 120 may receive various types of control command signals from the ultrasound imaging apparatus 200. That is, the type of data or a command which the communication unit 120 may exchange with the ultrasound imaging apparatus 200 through a wired/wireless signal is not limited.

The transducer 130 may be included in the ultrasound probe 100 as described above. The transducer 130 may emit an ultrasound signal to an object and receive an echo ultrasound signal reflected from the object. The transducer 130 has been described above and is thus not redundantly described here again. The transducer 130 which will be described below may be embodied as either a 2D transducer array or a 1D transducer array which may be operated in an altitude direction, and may thus emit a plane wave to the object.

The transducer 130 may sequentially emit a plane wave at various emission angles or in emission directions according to a control signal from the probe controller 140. An emission angle and an emission direction will be hereinafter referred to together as an emission angle when there is no need to differentiate them from each other.

For example, the transducer 130 may emit a plane wave at the same emission angle a plurality of times and at time intervals, emit the plane wave at different emission angles a plurality of times, or emit the plane wave at emission angles dependent on each other a plurality of times, according to a control signal from the probe controller 140, but embodiments are not limited thereto.

A region of an object, an image of which may be obtained from an ultrasound image may be the same or different according to an emission angle at which the plane wave is emitted by the transducer 130. The region of the object, an image of which may be obtained from the ultrasound image may be a region of the object to which at least three plane waves among a plurality of plane waves are emitted.

When a plane wave is emitted at the same emission angle a plurality of times, for example, when plane waves P1, P2, and P3 are emitted in parallel to an output plane of the 2D transducer array T2 as illustrated in FIGS. 9 and 10, a region of an object, an image of which may be obtained from an ultrasound image may be a region R1 to which these plane waves are emitted.

As another example, the transducer 130 may emit the plane waves P1, P2, and P3 at different emission angles according to a control signal as illustrated in FIGS. 11 and 12. In this case, a region of an object, an image of which may be obtained may be a region R2 in which the plane waves P1, P2, and P3 overlap one another. Thus, in one embodiment, a region of an object, an image of which may be obtained by the probe controller 140 is not limited to a plane parallel to a transducer array.

Referring to FIG. 6, the probe controller 140 may be included in the ultrasound probe 100.

The probe controller 140 may control overall operations of the ultrasound probe 100. The probe controller 140 may be embodied as at least one of a processor which may perform various processes, such as an image processing process and an operation processing process, and a graphic processor, or embodied as a single component having functions of the above-described processors.

The probe controller 140 may generate a control signal, and control overall operations of the elements of the ultrasound probe 100 using the generated control signal. For example, control data for controlling the elements of the ultrasound probe 100 and control data for performing an image processing process may be stored beforehand in the memory unit 150. The probe controller 140 may generate the control signal on the basis of the data stored in the memory unit 150, and control overall operations of the elements of the ultrasound probe 100 using the generated control signal. The memory unit 150 will be described in detail below.

The probe controller 140 may obtain an ultrasound image from an echo ultrasound signal received by the transducer 130. For example, the probe controller 140 may obtain the ultrasound image by performing an image processing process on the echo ultrasound signal received by the transducer 130 on the basis of the control data stored in the memory unit 150.

The ultrasound image may include a gray-scale image obtained by scanning an object according to an amplitude mode (A-mode), a brightness mode (B-mode), or a motion mode (M-mode).

Furthermore, the ultrasound image may include a Doppler image which expresses a motion of an object according to a Doppler mode using the Doppler effect. The Doppler image may be classified as a color Doppler image indicating blood flow, a tissue Doppler image indicating a motion of tissue, a spectral Doppler image indicating a moving speed of an object using a waveform, or the like, according to the type of the object to be diagnosed. Here, the color Doppler image may be referred to as a blood flow Doppler image.

For convenience of explanation, the color Doppler image indicating the flow of blood, i.e., blood flow, will be described below as an example of an ultrasound image, but embodiments which will be described below are not limited thereto and are applicable to all methods of obtaining an ultrasound image indicating a motion of an object.

The probe controller 140 may obtain a color Doppler image from a received echo ultrasound signal, and control the communication unit 120 to transmit the obtained color Doppler image to the ultrasound imaging apparatus 200. Thus, a tester may view the color Doppler image using the display unit 210 of the ultrasound imaging apparatus 200 to determine a blood flow speed or rate in a testee's blood vessel.

In order to more accurately express a motion of blood or tissue in a Doppler image, information regarding the speed of blood or the tissue and the speed of the blood or the tissue in each of directions is needed. Thus, as the above-described information is more accurately calculated, the precision of the Doppler image may be increased.

However, only a motion of an object at an angle at which an echo ultrasound signal is received may be determined from the echo ultrasound signal. In other words, only the motion of the object with respect to a normal of a plane parallel to a plane wave, i.e., in a vertical direction, may be determined from an echo ultrasound signal received by emitting the plane wave.

For example, the transducer 130 may emit a plane wave P4 at an emission angle θ with respect to x-y axes and an emission angle Φ with respect to x-z axes on the basis of a control signal from the probe controller 140, and receive an echo ultrasound signal reflected from an object, i.e., blood. In this case, the probe controller 140 may determine the speed of blood in a direction perpendicular to the plane wave P4 from the received echo ultrasound signal. Thus, the speed of blood in a direction in which blood flows, i.e., a direction of blood flow, cannot be accurately determined.

Thus, in order to obtain a 3D ultrasound image accurately reflecting a motion of an object, the speed of the motion of the object in various directions is needed to be measured. In particular, when blood flow is not uniform, for example, when blood flows in whirls, the speed of blood in each of directions should be accurately determined to conduct an accurate diagnosis.

In one embodiment, for a more accurate diagnosis, the ultrasound imaging system 1 may more quickly and accurately calculate not only the speed of blood flow but also the speed of blood flow in each of directions. A method of calculating a blood flow speed and a blood flow speed in each of directions will be described below.

Generally, a Doppler shift frequency of each of echo ultrasound signals received by emitting an ultrasound signal may be calculated by Equation 1 below.

$$f_d = \frac{2 \cdot f_0 \cdot v \cdot \cos A}{C} \quad \text{[Equation 1]}$$

Here, f0 represents the Doppler shift frequency, and f0 represents a main frequency of the ultrasound signal, i.e., a frequency of the emitted ultrasound signal. A represents an angle formed by the ultrasound signal and blood flow, i.e., an angle between a direction in which the ultrasound signal is emitted and a direction in which blood flows, v represents a blood flow speed, and C represents an ultrasonic velocity in an object, e.g., a living body.

An emission angle at which the ultrasound signal is emitted may be expressed using two angle parameters. For example, in a 3D space represented by x, y, and z axes, a first angle parameter may represent an emission angle of the ultrasound signal on the x-y axes, and a second angle parameter may represent an emission angle of the ultrasound signal on the x-z axes.

For example, referring to FIG. 13, the transducer 130 may emit the plane wave P4 at the emission angle θ with respect to the x-y axes and the emission angle Ψ with respect to the x-z axes, according to a control signal. Here, the first angle parameter may be the emission angle θ with respect to the x-y axes, and the second angle parameter may be the emission angle Ψ with respect to the x-z axes.

The transducer 130 may receive an echo ultrasound signal corresponding to the plane wave P4 with respect to a normal of the plane wave P4, i.e., in a vertical direction. In this case, a speed of an object which may be determined from a Doppler shift frequency inferred from the received echo ultrasound signal by the probe controller 140 may be the speed of the object in a direction of a normal vector D1 of the plane wave P4 illustrated in FIG. 13.

When blood flows at an angle α with respect to the x-y axes and an angle β with respect to the x-z axes, an angle A between an ultrasound signal and blood flow may be expressed as illustrated in FIG. 14. In this case, the Doppler shift frequency may be calculated by Equation 2 below.

$$f_d = \frac{2 \cdot f_0 \cdot v \cdot (\sin\beta\cos\phi - \cos\beta\sin\phi\cos(\alpha - \theta))}{C} \quad \text{[Equation 2]}$$

Here, the Doppler shift frequency may be based on the speed of blood flow in a direction of a vector perpendicular to the plane wave P4, e.g., the normal vector D1 of FIG. 13. Thus, the speeds of blood flow in various directions may be needed to determine the speed of blood flow in a direction in which blood actually flows.

For example, the speeds of blood flow in directions, e.g., the speed Vx of blood flow in an x-axis direction, the speed Vy of blood flow in a y-axis direction, and the speed Vz of blood flow in a z-axis direction, may be expressed by Equation 3 below. An ultrasound image may be more accurately obtained by determining the speed of blood flow in each of the directions.

$$v_x = v \cdot \cos\beta \cdot \cos\alpha, \; v_y = v \cdot \cos\beta \cdot \sin\alpha, \; v_z = -v \cdot \sin\beta \quad \text{[Equation 3]}$$

Referring to Equation 3, in order to determine the speed of blood flow in each of the directions, a blood flow speed v and directions in which blood flows, i.e., blood flow directions α and β, should be determined. Thus, a method of determining the blood flow speed v and the blood flow directions α and β from echo ultrasound signals received by emitting a plane wave at three different emission angles and then calculating the speed of blood flow in each of the directions on the basis of the blood flow speed v and the blood flow directions α and β will be described below.

The probe controller 140 may control the transducer 130 to sequentially emit a plurality of plane waves at different emission angles. In this case, the different emission angles are not limited provided they are different from each other.

The probe controller 140 may control the transducer 130 to emit a plane wave at different emission angles, and store information regarding the emission angles in the memory unit 150.

For example, the probe controller 140 may control the transducer 130 to emit to an object a first plane wave at an emission angle θ1 with respect to the x-y axes and an emission angle Ψ1 with respect to the x-z axes, a second plane wave at an emission angle θ2 with respect to the x-y axes and an emission angle Ψ2 with respect to the x-z axes, and a third plane wave at an emission angle θ3 with respect to the x-y axes and an emission angle Ψ3 with respect to the x-z axes.

For convenience of explanation, the emission angles θ1 and Ψ1 will be referred to as first emission angles, the emission angles θ2 and Ψ2 will be referred to as second emission angles, and the emission angles θ3 and Ψ3 will be referred to as third emission angles. In this case, the probe controller 140 may emit first to third plane waves such that at least one of x-y axis emission angles between the first emission angles, the second emission angles, and the third emission angles, and an x-z axis emission angle is different. In other words, first angle parameters of the first to third emission angles may be set to be different, and second angle parameters of the first to third emission angles may be set to be different.

The probe controller 140 may determine a Doppler shift frequency of each of first to third echo ultrasound signals received by sequentially emitting the first to third plane waves on the basis of Equation 2 above.

A first Doppler shift frequency inferred from the first echo ultrasound signal will be referred to as fd1. A second Doppler shift frequency inferred from the second echo ultrasound signal will be referred to as fd2. A third Doppler shift frequency inferred from the third echo ultrasound signal will be referred to as fd3.

When a plane wave is emitted three times, the probe controller 140 may individually infer the three first to third Doppler shift frequencies fd1, fd2, and fd3. For example, the probe controller 140 have determined beforehand emission angles of plane waves and thus equations related to the first to third Doppler frequencies fd1, fd2, and fd3 and including three unknowns v, α, and β may be inferred on the basis of Equation 2.

Thus, the probe controller 140 may calculate three unknowns, i.e., variables v, α, and β, from three equations through a simultaneous equation process. Accordingly, the probe controller 140 may determine a blood flow speed in each of directions through Equation 3 above while determining a blood flow speed. The probe controller 140 may obtain an ultrasound image accurately reflecting a motion of blood flow on the basis of the blood flow speed and the blood flow speed in each of the directions.

However, a method of calculating a blood flow speed, a blood flow speed in each of directions, etc. is not limited to the above-described method. A method of calculating a blood flow speed in each of directions from a plane wave emitted at an emission angle four times or more on the basis of a vector decomposition process and inferring a blood flow speed from the calculated blood flow speed in each of the directions will be described below.

The probe controller 140 may emit a plane wave at predetermined emission angles a plurality of times. In this case, the emission angles and a number of times of emitting the plane wave may be set beforehand. The emission angles may vary according to the number of times of emitting the plane wave, and the number of times of emitting the plane wave may be four or more.

In this case, the emission angles may be dependent on each other. For example, when a plane wave is emitted four times at the first emission angles θ1 and Ψ1, the second emission angles θ2 and Ψ2, the third emission angles θ3 and Ψ3, and fourth emission angles θ4 and Ψ4, the emission angles θ1 to θ4 on the x-y axes among the emission angles may be defined by the following Equation.

$$\theta_1=\theta°, \theta_2=(180-\theta)°, \theta_3=(180+\theta)°, \theta_4=(360-\theta)° \quad \text{[Equation 4]}$$

The emission angles φ1 to φ4 on the x-z axes among the emission angles may be defined by the following Equation.

$$\phi_1=\phi_2=\phi_3=\phi_4=\phi° \quad \text{[Equation 5]}$$

When the conditions of Equations 4 and 5 above are satisfied, a blood flow speed in the x-axis direction may be determined on the basis of the first to fourth Doppler shift frequencies, as expressed in Equation 6 below.

$$\frac{f_{d1}-f_{d2}-f_{d3}+f_{d4}}{-8\cdot\sin\phi\cdot\cos\theta\cdot f_0\cdot C}=v_x \quad \text{[Equation 6]}$$

A blood flow speed in the y-axis direction may be determined on the basis of the first to fourth Doppler shift frequencies, as expressed in Equation 7 below.

$$\frac{f_{d1}+f_{d2}-f_{d3}-f_{d4}}{-8\cdot\sin\phi\cdot\sin\theta\cdot f_0\cdot C}=v_y \quad \text{[Equation 7]}$$

A blood flow speed in the z-axis direction may be determined on the basis of the first to fourth Doppler shift frequencies, as expressed in Equation 8 below.

$$\frac{f_{d1}+f_{d2}+f_{d3}+f_{d4}}{-8\cdot\cos\phi\cdot f_0\cdot C} \quad \text{[Equation 8]}$$

That is, when a plane wave is emitted a plurality of times at specific emission angles dependent on each other, the relationship between a blood flow speed in each of the directions and the Doppler shift frequencies may be inferred from Equations 2 and 3, as expressed in Equations 6 to 8.

The final equations (6) to (8) include information on the three-dimensional vector of the blood flow, and include the velocity information about the X-axis, the Y-axis and the Z-axis of the blood flow. Accordingly, the probe controller 140 may more accurately generate the three-dimensional image based on the information about the three-dimensional vector.

In one embodiment, the probe controller 140 may quickly calculate a blood flow speed for each of vectors, i.e., in each of directions, through a small amount of calculation, and determine a blood flow speed on the basis of the calculated blood flow speed in each of the directions. Thus, the probe controller 140 may obtain an ultrasound image more accurately indicating a motion of blood on the basis of the calculated blood flow speed and the blood flow speed in each of the directions.

The memory unit 150 configured to store data may be included in the ultrasound probe 100. The memory unit 150 may be embodied as at least one type of storage medium among a flash memory type storage medium, a hard disk type storage medium, a multimedia card micro type storage medium, a card type memory (e.g., an SD or XD memory or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disc. However, the memory unit 150 is not limited thereto and may be embodied in any form known in the art.

For example, the memory unit 150 may store data regarding an echo ultrasound signal, data regarding an ultrasound image, etc. As another example, the memory unit 150 may store control data for controlling the elements of the ultrasound probe 100, control data for an imaging process of obtaining an ultrasound image, etc. but is not limited thereto.

The elements of the ultrasound probe 100 are not limited to those described above. For example, the ultrasound probe 100 may further include a display unit if necessary. The display unit may display information related to an operating state of the ultrasound probe 100, e.g., a power state of the ultrasound probe 100.

In addition, the ultrasound probe 100 may further include an input unit if necessary. The input unit may be embodied as a switch, a key, or the like as described above but is not limited thereto. A command to power on or off the ultrasound probe 100, etc. may be received from a user via the input unit. Furthermore, a control command to change an operating mode of the ultrasound probe 100 may be received via the input unit but embodiments are not limited thereto. An inner structure of the ultrasound imaging apparatus 200 will be described below.

Referring to FIG. 7, the ultrasound imaging apparatus 200 may include the display unit 210, the input unit 220, a communication unit 230, the main controller 240, and a memory unit 250. Here, at least one among the communication unit 230, the main controller 240, and the memory unit 250 may be integrated into an SoC embedded in the ultrasound imaging apparatus 200, and operated by a processor.

Since the number of SoCs included in the ultrasound imaging apparatus 200 is not limited to one and thus at least one among the communication unit 230, the main controller 240, and the memory unit 250 is not limited to being integrated into one SoC. The display unit 210 and the input unit 220 have been described above and are thus not redundantly described here.

The display unit 210 may display various types of information. For example, the display unit 210 may display an ultrasound image obtained from an echo ultrasound signal through an image processing process. In addition, when the display unit 210 is embodied as a touch screen type display, a graphical user interface (GUI) may be displayed on the display unit 210, through which various control commands related to not only the ultrasound imaging apparatus 200 but also the ultrasound probe 100 may be received from a user. Thus, the display unit 210 which is a touch screen type display may perform a function of the input unit 220.

The communication unit 230 may exchange data with an external device via a communication network. Here, the communication network includes a wired/wireless communication network. The wired/wireless communication network is as described above and is thus not described here again.

The communication unit 230 may exchange various signals with the ultrasound probe 100 via the communication network as described above. Referring to FIG. 9, in the ultrasound imaging system 1, the ultrasound probe 100 and the ultrasound imaging apparatus 200 are connected to each other via the communication unit 120 of the ultrasound probe 100 and the communication unit 230 of the ultrasound imaging apparatus 200 to exchange various data with each other. For example, the communication unit 230 may transmit various control commands and receive an echo ultrasound signal or a signal including ultrasound image data reconstructed from the echo ultrasound signal. In addition, the communication unit 230 may exchange various types of data with web storage or a cloud server via a wired/wireless communication network but is not limited thereto.

The ultrasound imaging apparatus 200 may include the main controller 240 which controls overall operations of the ultrasound imaging apparatus 200.

The main controller 240 may be embodied as at least one of a processor which may perform various processing processes such as an image processing process, an operation processing process, etc. and a graphic processor, or embodied as a single component having integrated functions of these processors.

The main controller 240 may generate a control signal, and control overall operations of the elements of the ultrasound imaging apparatus 200 using the generated control signal.

For example, control data for controlling the elements of the ultrasound imaging apparatus 200 and control data for performing an image processing process may have been stored in the memory unit 250. The main controller 240 may generate the control signal on the basis of the data stored in the memory unit 250, and control overall operations of the elements of the ultrasound imaging apparatus 200 using the generated control signal. The memory unit 250 will be described in detail below.

The main controller 240 may obtain an ultrasound image from an echo ultrasound signal received from the ultrasound probe 100. For example, the main controller 240 may obtain the ultrasound image by performing an image processing process on the received echo ultrasound signal on the basis of the control data stored in the memory unit 250. A method of obtaining an ultrasound image is as described above except that the method is performed by the main controller 240 other than the probe controller 140, and is thus not described in detail here.

Alternatively, the main controller 240 may control an ultrasound image received from the communication unit 120 of the ultrasound probe 100 to be displayed on the display unit 210.

The ultrasound imaging apparatus 200 may further include the memory unit 250 configured to store data. Similar to the memory unit 150 described above, the memory unit 250 may be embodied as, but is not limited to, already known various types of memories such as a flash memory type storage medium, a hard disk type storage medium, a multimedia card micro type storage medium, a card type memory (e.g., an SD or XD memory or the like), etc.

Various data may be stored in the memory unit 250. A digital signal or an analog signal corresponding to an echo ultrasound signal, data regarding an ultrasound image, etc. may be stored in the memory unit 250.

Control data for controlling the elements of the ultrasound imaging apparatus 200, control data for performing an image processing process on an echo ultrasound signal, etc. may be stored in the memory unit 250. Furthermore, data for implementing a graphical user interface displayed on the display unit 210 may be stored in the memory unit 250 but embodiments are not limited thereto.

A process of obtaining an ultrasound image from an echo ultrasound signal is as described above except that this process is performed by the main controller 240 of the ultrasound imaging apparatus 200 other than the probe controller 140 of the ultrasound probe 100, and is thus not described in detail here. Alternatively, a part of the process of obtaining an ultrasound image from an echo ultrasound signal may be performed by the probe controller 140 of the ultrasound probe 100 and another part of the process may be performed by the main controller 240 of the ultrasound imaging apparatus 200 but embodiments are not limited thereto.

A flow of an operation of an ultrasound imaging system will be briefly described below.

Figure 15:
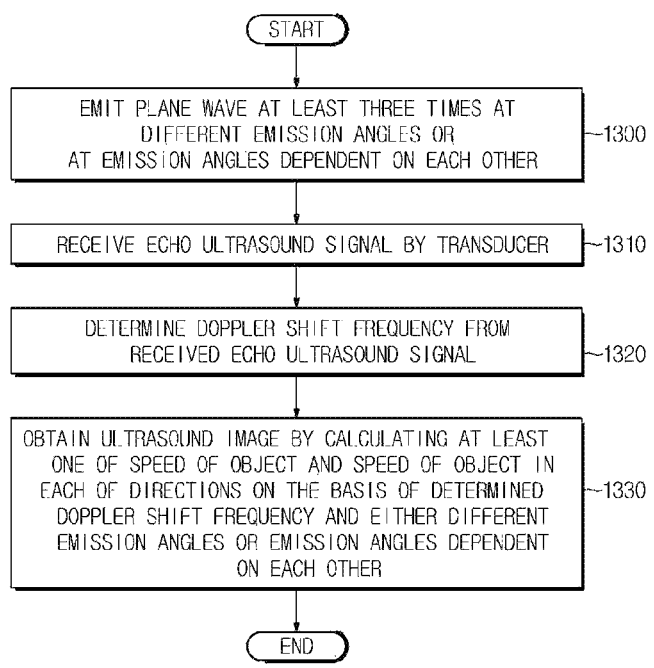
FIG. 15 is a flowchart of an operation of an ultrasound imaging system in accordance with an embodiment.

FIG. 15 is a flowchart of an operation of an ultrasound imaging system in accordance with an embodiment.

The ultrasound imaging system may emit a 2D ultrasound signal, e.g., a plane wave, using an ultrasound probe. In this case, the ultrasound imaging system may emit the plane wave at least three times either at different emission angles or at emission angles dependent on each other (1300). The emission angles have been described in detail above and are thus not described again here.

The ultrasound imaging system may receive an echo ultrasound signal reflected from a specific inner part of an object using the ultrasound probe (1310). The ultrasound imaging system may determine a Doppler shift frequency from the received echo ultrasound signal (1320).

In this case, the emission angles may be different in units of plane waves. For example, at least one of a first angle parameter and a second angle parameter representing the emission angles may be set to be different for each of the plane waves. Thus, the ultrasound imaging system may determine a Doppler shift frequency from each of received echo ultrasound signals.

A process of determining a Doppler shift frequency may be performed by at least one of the ultrasound probe 100 of FIG. 6 and the probe controller 140 of FIG. 6 as described above.

The ultrasound imaging system may calculate at least one of the speed of an object to be observed and the speed of the object in each of directions on the basis of the Doppler shift frequency and information regarding the emission angles, and obtain an ultrasound image on the basis of a result of the calculation (1330).

For example, when a plane wave is emitted three times at different emission angles, the ultrasound imaging system may infer three Doppler shift frequencies of an object, e.g., a speed of blood flow, a first angle parameter indicating a direction of blood flow and a second angle parameter of the blood flow which are included as unknowns. Here, the Doppler shift frequencies may be equations including as unknowns the first angle parameter indicating the speed and direction of the blood flow and the second angle parameter of the blood flow.

Here, the first angle parameter of the blood flow may indicate an angle at which blood flows on the x-y axes in a 3D space represented by x, y, and z axes, and the second angle parameter of the blood flow may indicate an angle at which blood flows on the x-z axes.

The ultrasound imaging system may calculate the speed of blood flow and the speed of blood flow in each of directions by determining the speed of the blood flow and the first and second angle parameters of the blood flow from three Doppler shift frequencies inferred through a simultaneous equation process, and obtain an ultrasound image more accurately reflecting a motion of blood on the basis of a result of the calculation.

As another example, when a plane wave is emitted four times or more at emission angles dependent on each other, the relationship between the emission angles, a Doppler shift frequency, and the speed of blood flow in each of directions may be determined beforehand. In one embodiment, as shown in Equations 6 to 8, the speed of blood flow in each of directions may be represented according to the Doppler shift frequency and the emission angles.

Accordingly, the ultrasound imaging system may more quickly calculate the speed of blood flow in each of directions from three Doppler shift frequencies, and may also quickly calculate the speed of blood flow. The ultrasound imaging system may quickly obtain an ultrasound image through a small amount of calculation on the basis of the speed of blood flow in each of the directions and the speed of blood flow, thereby enabling a tester to quickly diagnose an object.

Methods in accordance with embodiments may be written as program commands executable via any computer means and recorded in a computer-readable recording medium. The computer-readable recording medium may include a program command, a data file, and a data structure solely or in combination. The program commands recorded on the computer-readable recording medium may be specifically designed and configured for the embodiments, or may be well known to and usable by one of ordinary skill in the art of computer software. Examples of the computer-readable recording medium include magnetic media (e.g., hard disks, floppy disks, and magnetic tapes), optical media (e.g., CD-ROMs and DVDs), magneto-optical media (e.g., floptical disks), and hardware devices specifically configured to store and execute program commands (e.g., ROMs, RAMs, and flash memories). Examples of program commands include not only machine language codes prepared by a compiler, but also high-level language codes executable by a computer by using an interpreter. The hardware device may be configured to operate as at least one software module to perform operations of methods, or vice versa.

While embodiments have been described above with respect to specific examples and drawings, various changes and modification may be made therein by one of ordinary skill in the art. For example, an appropriate result may be achieved even when the techniques described herein are performed in an order different from that of the above-described methods, and/or when the elements of the systems, structures, apparatus, circuits, etc. described above are coupled or combined with each other unlike in the above-described methods or are replaced with other elements or equivalents thereof.

Accordingly, it should be understood that modifications, alternatives, other embodiments, and equivalents of the claims are within the scope of the following claims.

The invention claimed is:

1. An ultrasound probe comprising:
a transducer configured to receive an echo ultrasound signal by emitting a plane wave at least three times either at different emission angles or at emission angles which are dependent on each other; and
a probe controller configured to obtain an ultrasound image by determining a Doppler shift frequency from the received echo ultrasound signal and calculating at least one of a speed of an object and a speed of the object in each of directions on the basis of the determined Doppler shift frequency and either the different emission angles or the dependent emission angles,
wherein the different emission angles or the dependent emission angles are represented by two angle parameters.

2. The ultrasound probe according to claim 1, wherein the probe controller controls the transducer to emit the plane wave at least three times at the different emission angles, determines the Doppler shift frequency from the echo ultrasound signal received by emitting the plane wave at least three times, calculates a blood flow speed and direction of the object on the basis of the determined Doppler shift frequency and the different emission angles, and obtains the ultrasound image on the basis of the calculated blood flow speed and direction of the object.

3. The ultrasound probe according to claim 1, wherein the probe controller controls the transducer to emit the plane wave at least four times at the dependent emission angles, determines the Doppler shift frequency from the echo ultrasound signal received by emitting the plane wave at least four times, determines a blood flow speed of the object in each of the directions on the basis of the determined Doppler shift frequency and the dependent emission angles, and obtains information regarding a blood flow speed of the object on the basis of the blood flow speed of the object in each of the directions.

4. The ultrasound probe according to claim 1,
wherein the two angle parameters of each of the different emission angles are set to be different from those of the other emission angles.

5. The ultrasound probe according to claim 1,
wherein one of the two angle parameters of each of the dependent emission angles is set to be the same as ones of the two angle parameters of the other emission angles.

6. The ultrasound probe according to claim 1,
wherein one of the two angle parameters of each of the dependent emission angles is set to be the same as ones of the two angle parameters of the other emission angles, and
the other angle parameter of each of the dependent emission angles is set to be spaced apart from the other angle parameters of the other emission angles according to a predetermined angle.

7. An ultrasound imaging apparatus comprising:
a transceiver configured to receive an echo ultrasound signal reflected from an object when a plane wave is emitted at least three times either at different emission angles or at emission angles which are dependent on each other; and
a main controller configured to obtain an ultrasound image by determining a Doppler shift frequency from the received echo ultrasound signal and calculating at least one of a speed of an object and a speed of the object in each of directions on the basis of the determined Doppler shift frequency and either the different emission angles or the dependent emission angles,
wherein the different emission angles or the dependent emission angles are represented by two angle parameters.

8. The ultrasound imaging apparatus according to claim 7, wherein the main controller controls the transceiver to transmit a control signal for emitting the plane wave at least three times at the different emission angles, determines the Doppler shift frequency from the received echo ultrasound signal, calculates a blood flow speed and direction of the object on the basis of the determined Doppler shift frequency and the different emission angles, and obtains the ultrasound image on the basis of the calculated blood flow speed and direction of the object.

9. The ultrasound imaging apparatus according to claim 7, wherein the main controller controls the transceiver to transmit a control signal for emitting the plane wave at least four times at the dependent emission angles, determines the Doppler shift frequency from the received echo ultrasound signal, determines a blood flow speed of the object in each of the directions on the basis of the determined Doppler shift frequency and the dependent emission angles, and obtains information regarding a blood flow speed of the object on the basis of the determined blood flow speed of the object in each of the directions.

10. The ultrasound imaging apparatus according to claim 7,
wherein the two angle parameters of each of the different emission angles are set to be different from those of the other emission angles.

11. The ultrasound imaging apparatus according to claim 7,
wherein one of the two angle parameters of each of the dependent emission angles is set to be the same as ones of the two angle parameters of the other emission angles.

12. The ultrasound imaging apparatus according to claim 7,
wherein one of the two angle parameters of each of the dependent emission angles is set to be the same as ones of the two angle parameters of the other emission angles, and
the other angle parameter of each of the dependent emission angles is set to be spaced apart from the other angle parameters of the other emission angles according to a predetermined angle.

13. A method of controlling an ultrasound imaging apparatus, comprising:
receiving an echo ultrasound signal reflected from an object when a plane wave is emitted at least three times either at different emission angles or at emission angles which are dependent on each other; and
obtaining an ultrasound image by determining a Doppler shift frequency from the received echo ultrasound signal and calculating at least one of a speed of an object and a speed of the object in each of directions on the basis of the determined Doppler shift frequency and either the different emission angles or the dependent emission angles,
wherein the different emission angles or the dependent emission angles are represented by two angle parameters.

14. The method according to claim 13, wherein the obtaining of the ultrasound image comprises determining the Doppler shift frequency from the received echo ultrasound signal, calculating a blood flow speed and direction of the object on the basis of the determined Doppler shift frequency and the different emission angles, and obtaining the ultrasound image on the basis of the calculated blood flow speed and direction of the object.

15. The method according to claim 13,
wherein the two angle parameters of each of the different emission angles are set to be different from those of the other emission angles.

* * * * *